US009861499B2

(12) United States Patent
Sensinger

(10) Patent No.: US 9,861,499 B2
(45) Date of Patent: Jan. 9, 2018

(54) GRIPPING DEVICE WITH SWITCHABLE OPENING MODES

(71) Applicant: Rehabilitation Institute of Chicago, Chicago, IL (US)

(72) Inventor: Jonathon Sensinger, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 14/030,095

(22) Filed: Sep. 18, 2013

(65) Prior Publication Data

US 2014/0081425 A1   Mar. 20, 2014

Related U.S. Application Data

(60) Provisional application No. 61/702,642, filed on Sep. 18, 2012.

(51) Int. Cl.
*A61F 2/56* (2006.01)
*A61F 2/58* (2006.01)
*B25J 9/10* (2006.01)
*A61F 2/54* (2006.01)

(52) U.S. Cl.
CPC ............. *A61F 2/586* (2013.01); *A61F 2/588* (2013.01); *B25J 9/104* (2013.01); *A61F 2/54* (2013.01)

(58) Field of Classification Search
CPC .......... A61F 2/588; A61F 2/583; A61F 2/586; A61F 2/54; A61F 2/68; A61F 2002/587; B25J 15/08; B25J 15/0028; B25J 9/104
USPC ........................................ 623/57–58, 63, 65
See application file for complete search history.

(56) References Cited

U.S. PATENT DOCUMENTS

| 2,557,792 A | * | 6/1951 | Maguth ........................... 623/57 |
| 4,280,265 A | | 7/1981 | Murphy |
| 4,476,750 A | | 10/1984 | Murphy |
| 4,990,162 A | * | 2/1991 | LeBlanc et al. ................. 623/63 |
| 5,219,366 A | | 6/1993 | Scriber |

(Continued)

FOREIGN PATENT DOCUMENTS

DE           901583       *  1/1954   .................. 623/57

OTHER PUBLICATIONS

The Open Prosthetics Project. Body-Powered Hook. Jul. 27, 2011 (Verified by the Wayback Machine).*

(Continued)

*Primary Examiner* — Thomas J Sweet
*Assistant Examiner* — Christie Bahena
(74) *Attorney, Agent, or Firm* — Polsinelli PC; Ari M. Bai

(57) ABSTRACT

A gripping device that comprises a first moveable jaw and a second fixed jaw is disclosed. The gripping device has a handle operatively engaged to the first moveable jaw and a connecting link operatively engaged to the first moveable jaw. The connecting link is positioned in at least one of a first position or a second position. The change in the position of the connecting link allows the gripping device to have either a default closed position or a default open position, which can be defined by voluntarily-open or voluntary-close modes of operation, respectively. The first moveable jaw moves in either of the modes of operation. The change in the mode of operation is accomplished through use of a connecting link that is passed through a singularity during the switching process to achieve the different output positions and directions.

26 Claims, 4 Drawing Sheets

(56) References Cited

U.S. PATENT DOCUMENTS

| | | | |
|---|---|---|---|
| 5,800,571 A * | 9/1998 | Carlson et al. | 623/57 |
| 6,010,536 A | 1/2000 | Veatch | |
| 7,341,295 B1 * | 3/2008 | Veatch et al. | 294/106 |
| 7,867,287 B2 | 1/2011 | Puchhammer | |
| 8,257,446 B2 | 9/2012 | Puchhammer | |
| 8,343,234 B2 | 1/2013 | Puchhammer | |
| 8,579,991 B2 | 11/2013 | Puchhammer | |
| 8,690,963 B2 | 4/2014 | Puchhammer | |
| 2006/0167562 A1 * | 7/2006 | Williams et al. | 623/24 |

OTHER PUBLICATIONS

Ottobock VariPlus Speed Hand. Ottobock Healthcare Products GmbH. Nov. 2008. p. 1.*

Sullivan, Timothy. Teh, Swok Siong. Design and Fabrication of a Hybrid Body-Powered Prosthetic Hand with Voluntary Opening and Voluntary Closing Capabilities. ASME 2011 International Mechanical Engineering Congress and Exposition. vol. 2, pp. 155-162. Nov. 11-17, 2011.*

Open Prosthetics Project Wiki, Updating the APRL Hook, printed on Jan. 27, 2015 from http://openprosthetics.wikispot.org/updating_the_aprl_hook, 13 pages.

The Open Prosthetics Projects, An Initiative of the Shared Design Alliance, printed on Jan. 27, 2015 from http://openprosthetics.org/body-powered, 5 pages.

TRS Inc., Adult Grip Prehensors, printed on Jan. 27, 2015 from http://www.trsprosthetics.com/adults/grip_prehensors.asp, 2 pages.

TRS Inc., ADEPT Prehensors, printed on Jan. 27, 2015 from http://www.trsprosthetics.com/children/adept_prehensors.asp, 2 pages.

Toughware Prosthetics product information printed on Jan. 27, 2015 from http://www.jmsplastics.com/prosthetic/toughware.php, 2 pages.

Biddiss, Upper limb prosthesis use and abandonment: A survey of the last 25 years. Prosthet Orthot Int, 2007, 31:236-257.

Cupo, Clinical Evaluation of a New, Above-Elbow, Body-Powered Prosthetic Arm: A Final Report. Journal of Rehabilitation Research and Development, 1998, 35:431-446.

Frey, Voluntary-Opening Prehensors with Adjustable Grip force. Journal of Prosthetics and Orthotics, 1995 7:124-131.

Fryer, Body-Powered Components. In: Atlas of Amputations and Limb Deficiencies, 2004, (Smith, D. G. et al., eds), pp. 131-143 Rosemont, IL: American Academy of Orthopaedic Surgeons.

LeBlanc, New designs for prosthetic prehensors. Proceedings of 9th International Symposium on External Control of Human Extremities; 1987; Dubrovnik, Yugoslavia. p. 475-81.

Meeks, Preliminary assessment of three new designs of prosthetic prehensors for upper limb amputees. Prosthet Orthot Int.,1988; 12(1):41-45.

Pinzur, Functional outcome following traumatic upper limb amputation and prosthetic limb fitting. J Hand Surg-Am, 1994, 19:836-839.

Plettenburg, The WILMER Appealing Prehensor. Journal of Prosthetics and Orthotics, 2006, 18:43-45.

Plettenburg, Voluntary closing: A promising opening in hand prosthetics. Technology and Disability, 2003, 15:85-94.

Procter, Clinical Evaluation of a New Design Prosthetic Prehensor. Journal of Prosthetics and Orthotics, 1991, 3:79-83.

Sensinger, Voluntary Opening-Closing Terminal Device Design poster presentation and abstract. Proceedings of the 13th International Conference on Prosthetics and Orthotics; 2010; Leipzig, Germany.

Sullivan, Design and fabrication of a hybrid body-powered prosthetic hand with voluntary opening and voluntary closing capabilities. In: ASME International Mechanical Engineering Congress and Exposition, 2011, pp. 1-8 Denver, CO.

Veatch, A combination VO/VC terminal device with variable mechanical advantage, American Academy of Orthotics and Prosthetics, 2004, 5 pgs.

Weir, Design of Artificial Arms and Hands for Prosthetic Applications. In: Standard Handbook of Biomedical Engineering and Design, 2003, (Kutz, M., ed), Chapter 32. New York: McGraw-Hill.

Weir, Design of Artificial Arms and Hands for Prosthetic Applications. In: Biomedical Engineering and Design Handbook, 2009, (Kutz, M., ed), 75 pages, New York: McGraw-Hill.

Jonathon Sensinger, Voluntary Opening-Closing Terminal Device Design, Proceedings of the 13th International Conference on Prosthetics and Orthotics, Leipzig, Germany, 2010. 2 pages.

* cited by examiner

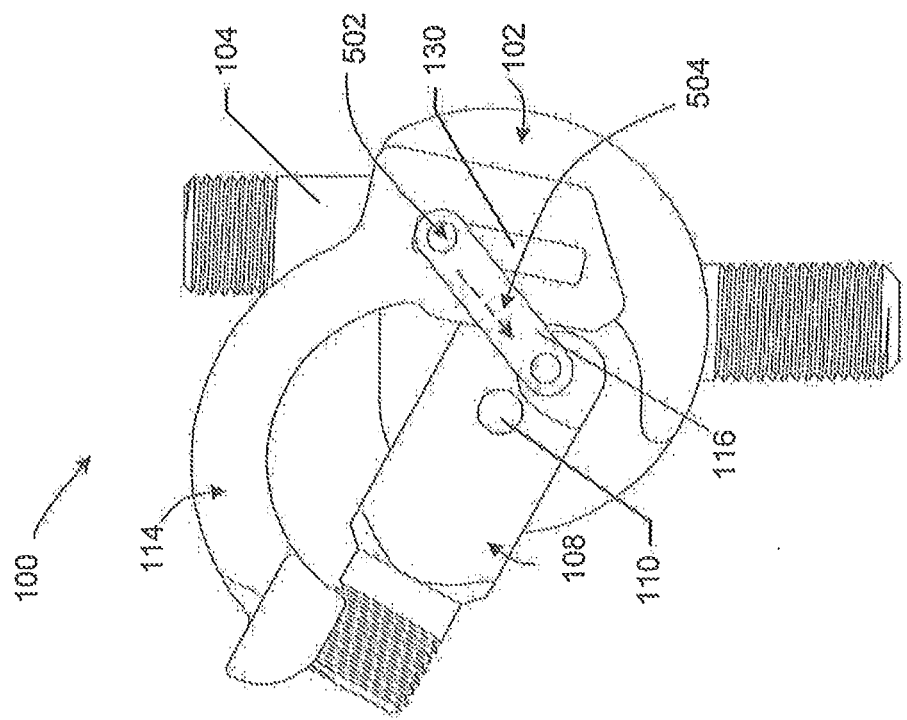
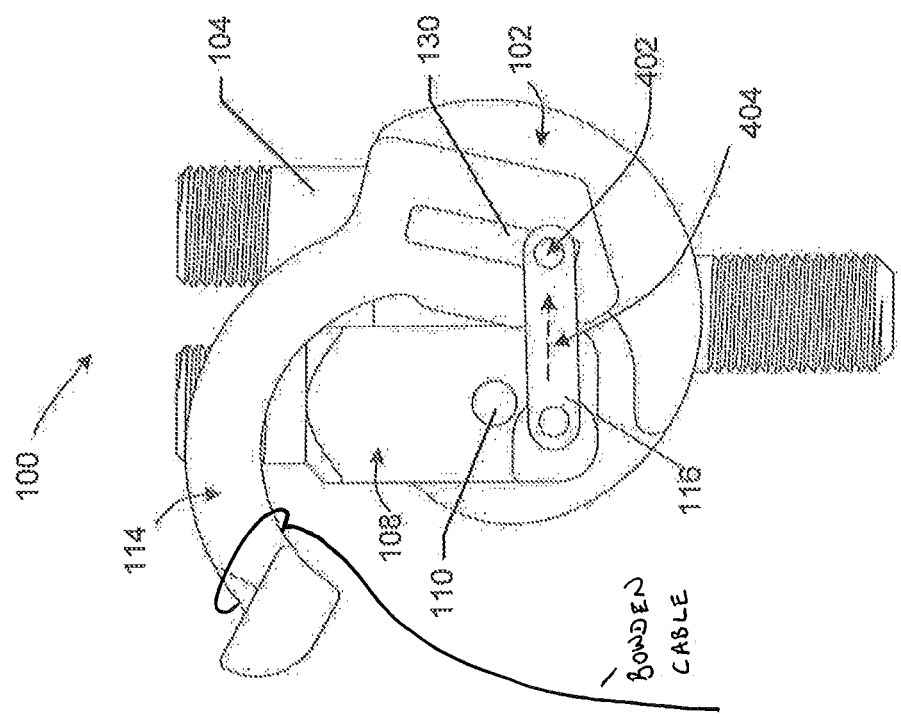

GRIPPING DEVICE WITH SWITCHABLE OPENING MODES

CROSS REFERENCE TO RELATED APPLICATIONS

This application is a non-provisional that claims benefit to U.S. Provisional Patent Application No. 61/702,642 filed on Sep. 18, 2012, which is herein incorporated by reference in its entirety.

FIELD

The present document relates generally to prosthetics and in particular, to a gripping device for a prosthesis having switchable open and close modes of operation.

BACKGROUND

An estimated 41,000 people in the United States live with an upper limb loss at or above the wrist. The loss of a limb by an individual can profoundly limit everyday activities such as dressing, eating, and performing personal hygiene tasks. The loss of a limb may also affect social interactions and personal relationships and in some cases can threaten the basic independence of the individual. Further, the individual can experience difficulty in grasping and holding objects which may impede leisure activities, such as reading or playing sports. The inability to properly operate a prosthetic by the individual may also prevent performance of certain employment tasks or severely limit future job prospects, thereby impacting a person's financial security, sense of identity and purpose, and overall quality of life.

Conventional passive prosthetic devices may be very lightweight and relatively inexpensive to manufacture; however, such prosthetic devices provide very limited function. Body-powered devices are generally light, robust, functional, and inexpensive. The majority of these devices have a voluntary-open (VO) mode of operation, while several others have a voluntary-closing (VC) mode of operation. A few devices have both a VO and a VC mode of operation. However, these devices are complex and require altering the initial positions of the jaws and the direction of movement, without altering the direction of movement and starting position of a Bowden cable attachment. As such, there remains a need for a gripping device or similar prosthetic device that can quickly and easily switch between voluntary-open and voluntary modes of operation without extensive adjustments.

SUMMARY

In one embodiment, a gripping device may include a first movable jaw and a second fixed jaw. The gripping device includes a handle operatively engaged to the first movable jaw. A connecting link is operatively engaged to the first moveable jaw. The connecting link is positioned in at least one of a first position or a second position. In the first position, the connecting link causes the first moveable jaw to move inwardly relative to the second fixed jaw when the handle is moved inwardly, while in the second position the connecting link causes the first moveable jaw to move outwardly relative to the second fixed jaw when the handle is moved inwardly. In either position, an equilibrium position of the handle remains the same when the connecting link is in the first position or in second position.

In another embodiment, a gripping device may include a first moveable jaw and a second fixed jaw. The gripping device also includes a handle operatively engaged to the first moveable jaw. In addition, a connecting mechanism is operatively engaged to the first moveable jaw. The connecting mechanism is positioned in at least one of a first position or a second position. In the first position, the connecting mechanism causes the first moveable jaw to move inwardly relative to the second fixed jaw when the handle is moved inwardly, while in the second position the connecting mechanism causes the first moveable jaw to move outwardly relative to the second fixed jaw when the handle is moved inwardly. The connecting mechanism causes the alternating movements of the first moveable jaw by imparting a force on the first moveable jaw through a singularity. As used herein, a singularity refers to point along a mechanical linkage wherein the motion of the jaw on one side of the singularity is different in response to the same motion of the handle on the other side of the singularity.

In another embodiment, the mechanism includes one or more hydraulic channels operatively engaged to the first moveable jaw for causing the first moveable jaw to open relative to the second fixed jaw when the handle is moved inwardly or alternately causing the first moveable jaw to close relative to the second fixed jaw when the handle is moved inwardly. The alternating movement of the first moveable jaw is accomplished by directing the flow of fluid through alternating hydraulic channels on either side of a singularity, causing a reversal in movement about the pivot.

In another embodiment, a cable is used as the mechanism that is operatively engaged to the first movable jaw for alternately causing the first moveable jaw to move inwardly or outwardly relative to the second fixed jaw when the handle is moved inwardly. The alternating movement of the first moveable jaw is accomplished by passing a cable through a singularity.

Additional objects, advantages, and novel features of the invention shall be set forth in part in the description that follows, and in part will become apparent to those skilled in the art upon examination of the following or may be learned by practice of the invention. The objects and the advantages may be realized and attained by means of the instrumentalities and in combinations particularly pointed out in the appended claims.

BRIEF DESCRIPTION OF THE DRAWINGS

FIG. 8 depicts the gripping device in the voluntary-open mode of operation.

FIG. 9 depicts the gripping device in a voluntary-close mode of operation.

Corresponding reference characters indicate corresponding elements among the view of the drawings. The headings used in the figures should not be interpreted to limit the scope of the claims.

DETAILED DESCRIPTION

As described herein, the gripping device of the present disclosure is a device that may be switched between a voluntary-open (VO) mode of operation and a voluntary-close (VC) mode of operation. When in the VO mode of operation, a user actuates one or more handles of the gripping device to open the jaws of the device. When released, the handles of the device return to a default position, which in turn causes the jaws of the gripping device to return to a default position so that jaws can be used to grasp an object using the force provided by a biasing component, such as a spring or elastic band.

When in the VC mode of operation, a user must actuate a portion of the gripping device to close the jaws of the device. This allows the user to determine the pinch or compressive force to apply to an object. However, if the user discontinues applying the force, the jaws of the device will normally return to the default position and release the grip on a held object.

In one embodiment, the gripping device may include a movable jaw and a fixed jaw. In other embodiments, the gripping device may include any number and/or combination of movable jaws and fixed jaws. In all embodiments, the gripping device can easily switch between the VO and VC modes of operation by a variety of switching mechanisms. In one embodiment, the movable jaw may open or close while the fixed jaw remains stationary regardless of which mode of operation is selected.

The gripping device may also be used as a prehensor device. In various embodiments, the gripping device may be used as a prosthetic hand or terminal device. Moreover, the gripping device may also be used as or incorporated into tools, such as pliers and wrenches.

Figure 1:
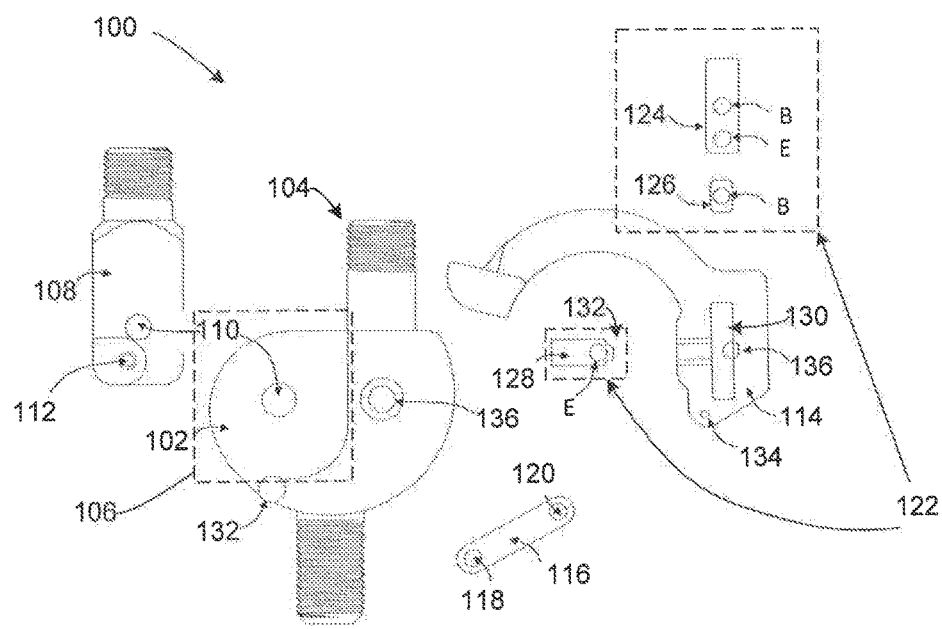
FIG. 1 is an exploded view of a gripping device according to one embodiment.
Figure 2:
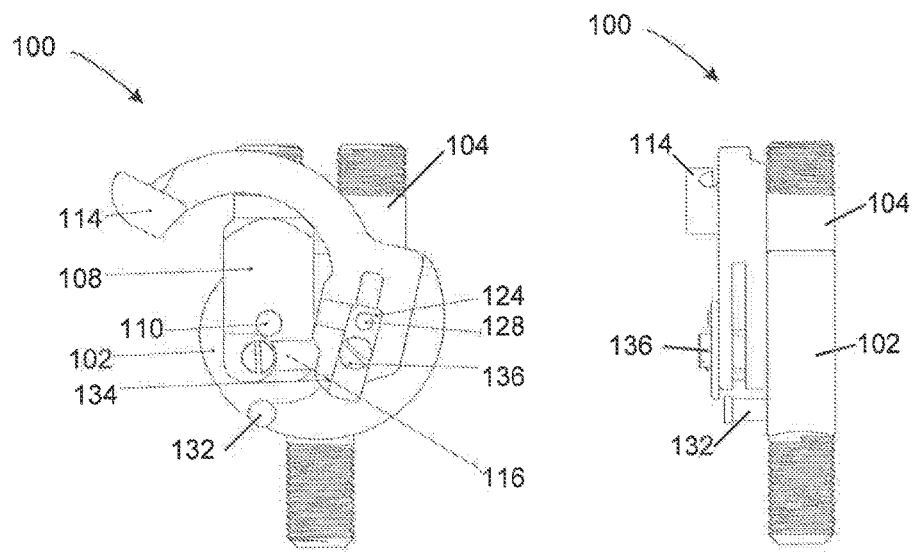
FIG. 2 is a plan view of the gripping device according to one embodiment.
Figure 3:
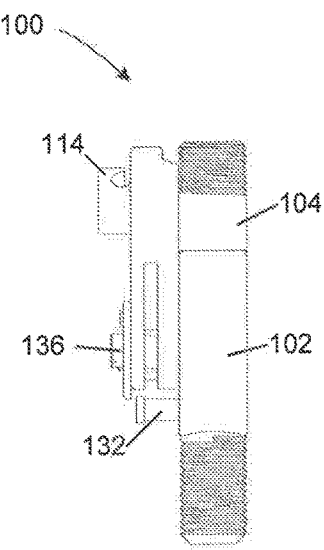
FIG. 3 is a side plan view of the gripping device according to one embodiment.

Referring now to FIGS. 1-3, an embodiment of the gripping device, designated 100, is shown. In some embodiments, the gripping device 100 may include a main body 102 that includes a fixed jaw 104 and recessed section 106, positioned adjacent to the fixed jaw 104, for receiving a movable jaw 108.

The moveable jaw 108 is rotatably engaged to the main body 102 at a pivot joint 110. In some embodiments, the moveable jaw 108 can be connected to the main body 102 using any suitable fastening means or fastening arrangement, including but not limited to a pin 112, such that movable jaw may rotate towards and away relative to the fixed jaw 104 about the pivot joint 110.

The moveable jaw 108 includes a drive joint 112 that is used to operatively link the moveable jaw 108 with a drive handle 114 through a mechanism, such as a connecting link 116. For example, a distal end 118 of the connecting link 116 is engaged to drive joint 112, such that lateral translation of the connecting link 116 causes the moveable jaw 108 to pivot about the pivot joint 110. In some embodiments, the proximal end 120 of the connecting link 116 is engaged to a switch assembly 122 of the drive handle 114. As such, rotation or other movement of the drive handle 114 causes the lateral translation of the connecting link 116, which in turn causes the movable jaw 108 to pivot. In various other embodiments, the mechanism illustrated by the connecting link 116 may be hydraulically powered or cable-driven.

The drive handle 114 acts as an actuation handle that switches the gripping device 100 between the voluntary-open and voluntary-close modes of operation. In one embodiment, the drive handle 114 may be actuated using a Bowden cabling system known in the art. In other embodiments, that drive handle 114 may be actuated by any other means to impart a mechanical force on the drive handle 114. The drive handle 114 is rotatably engaged to the main body 102 through a pivot 136. In various embodiments, a spring (not shown) is connected between pins 132 and 134 to apply a biasing force on the drive handle 114 that returns the drive handle 114 to a default position. In other embodiments, alternative equilibrium arrangements, including but not limited to those that use torsion springs or magnets, may be used to maintain a default equilibrium of the movable jaw 108 or the drive handle 114. In addition, the magnitude of the forces exerted by the movable jaw 108 in the different modes of operation could be modified by varying the attachment locations of any biasing springs (not shown), or by the use of one or more additional springs.

In one embodiment, the switch assembly 122 of the drive handle 114 may be a bi-stable switch that includes a position knob 124, a vertical linear guide 126, and a horizontal linear guide 128. The vertical guide 124 is constrained to move vertically within a channel 130 of the switch assembly 122, while the horizontal linear guide 128 is constrained to move horizontally within the channel 130. A magnet 132 embedded in the drive handle 114 exerts a force that is proportional to the distance defined by the channel 130 on the horizontal linear guide 128 relative to the switch assembly 122. The force exerted by the magnet 132 provides stability to minimize undesired movement of the switch assembly 122 while defining two stable orientations for the orientation of the position knob 124. The position knob 124 is therefore movable between a "vertical up" orientation and a "vertical down" orientation.

In other embodiments, the switch assembly 122 may be a reciprocating switch mechanism, such as those used in retractable ballpoint pens or the switch assembly may use bicycle-indexed gear shifters to achieve the bi-stable positions of the connecting link 116.

The orientation of the position knob 124 determines the direction of motion for the connecting link 116 when the drive handle 114 is actuated. As such, the orientation of the position knob 124 determines the mode of operation for the gripping device 100.

Figure 4:
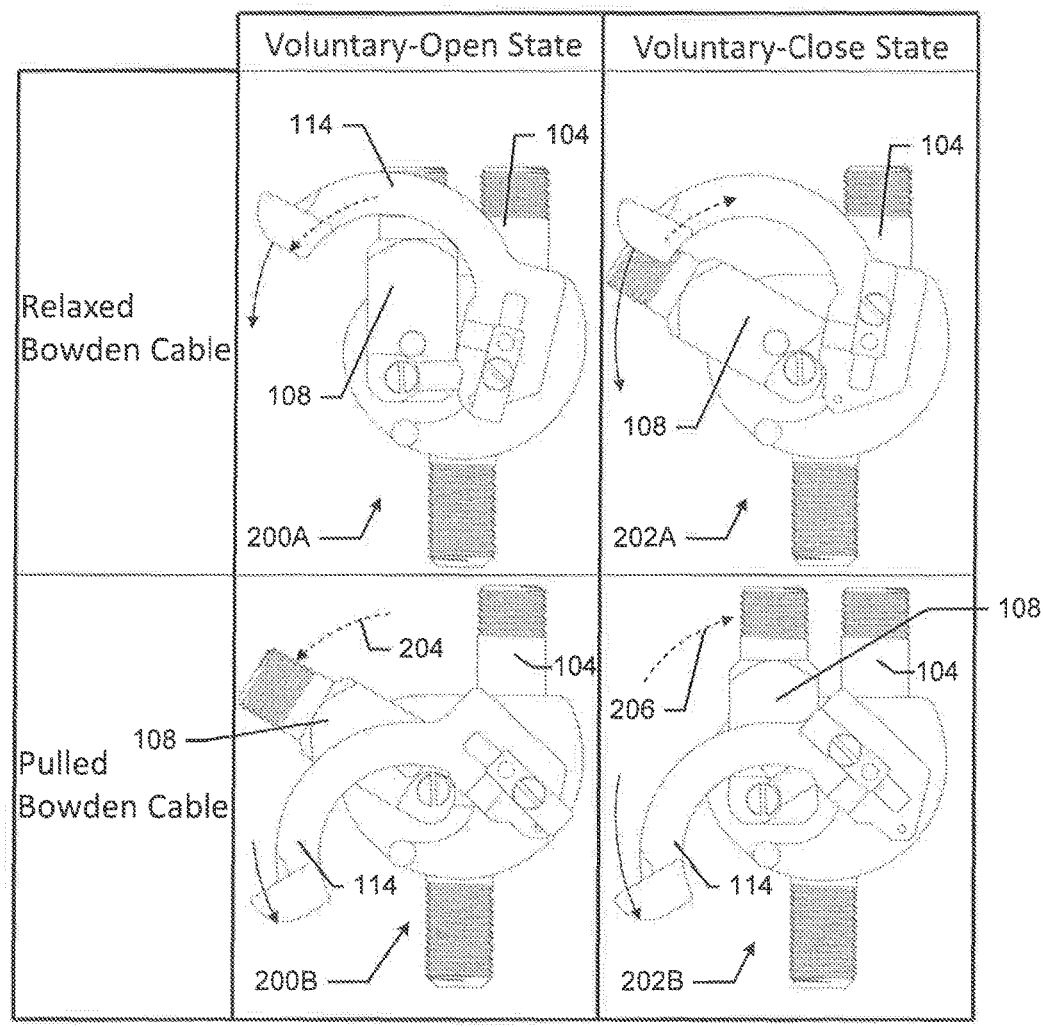
FIG. 4 illustrates an embodiment of the gripping device in a voluntary-open mode of operation and a voluntary-close mode of operation.

Referring now to FIG. 4, the mode of operation will determine whether force applied to the drive handle 114 will cause the movable jaw 108 to open or rotate away, as indicated by arrow 204, from the fixed jaw 104, as shown in the voluntary-open mode of operation at positions 200A and 200B. Conversely, when the mode of operation for the gripping device 100 is in a voluntary-close mode of operation, shown at positions 202A and 202B, actuation of the drive handle 114 will cause the movable jaw 108 to close or rotate towards the fixed jaw 104, as indicated by arrow 206.

Figure 7:
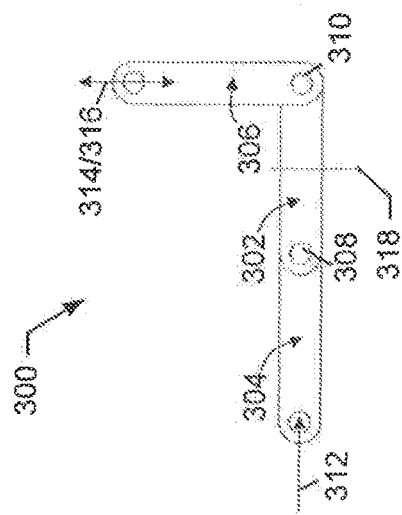
FIGS. 5-7 depict the motion of linkages through a singularity.
Figure 6:
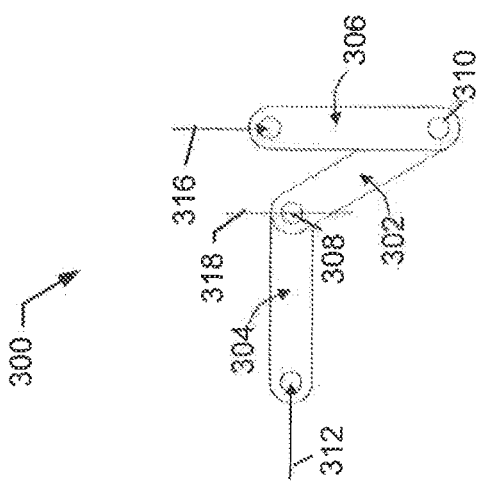
Figure 5:
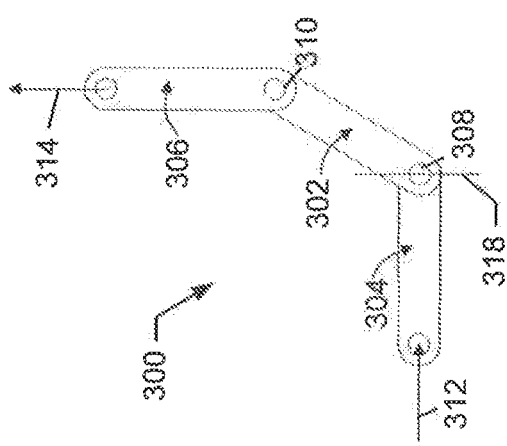

A conceptual depiction of the translation of one embodiment of a linkage system 300 is shown in FIGS. 5-7. An intermediate link 302, which is used to illustrate the translation of the connecting link 116, is pivotally engaged to an input link 304, which is used to illustrate the input force applied by actuation of the drive handle 114 at a first pivot point 308. The intermediate link 302 is also pivotally engaged to a drive link 306, at a second pivot point 310. The drive link 306 is used to illustrate the motion of the movable jaw 108. As such, FIGS. 5-7 depict the motion of the links through a singularity 318, such that on either side of the singularity 318, the motion of the drive link 306 varies in response to the same motion of the input link 304. In FIGS. 5-7, the singularity 318 refers to a point within the linkage system 300, wherein the motion of the drive link 306 on one side of the singularity 318 is different in response to the same motion of the input link 304 on the other side of the singularity 318.

Similar to the limited motions of the connecting link 116 and the drive handle 114, in one embodiment, the input link 304 is constrained to vertical movement, while the drive link 306 is constrained to horizontal movement.

FIG. 5 illustrates the linkage system 300 on one side of the singularity 318. When a force 312 is applied to the input link 304, the resulting translation of the drive link 306, is an upward vertical motion 314. Similarly, FIG. 6 illustrates the motion of the linkage system 300 on the other side of the singularity 318. As shown, when the force 312 is applied to the input link 304, the resulting translation of the drive link 306 is a downward vertical motion 316. The different orientations of the intermediate link 302 correspond to the different orientations of the position knob 124 within the switch assembly 122, which corresponds to the different modes of operation for the gripping device 100. As shown, the applied force 312 is often in the same direction, but the resulting motion and orientation of the drive link 306 may differ. FIG. 7 illustrates the linkage system 300 at the point of singularity 318. As such, when the force 312 is applied to the input link 304, the drive link 306 may move in either the upward vertical motion 314 or the downward vertical motion 316.

FIGS. 8-9 illustrate the gripping device 100 in the voluntary-open mode of operation configuration and the voluntary-close mode of operation configuration, respectively. In particular, the orientation of the connecting link 116 relative to the drive handle 114 in each mode of operation is shown. Referring to FIG. 8, the proximal end of the connecting link 116 is positioned at a lower region 402 of the channel 130 within the drive handle 114. When the drive handle 114 is actuated, the connecting link 116 moves generally towards the fixed jaw 104, as indicated by arrow 404. This causes the movable jaw 108 to pivot about pivot point 110 and open away from the fixed jaw 104.

Conversely, as shown in FIG. 9 the proximal end of the connecting link 116 is positioned at an upper region 502 of the channel 130 within the drive handle 114. When the drive handle 114 is actuated, the connecting link 116 moves generally away the fixed jaw 104, as indicated by arrow 504. This action causes the movable jaw 108 to pivot about pivot point 110 and close towards the fixed jaw 104. As shown, the starting position and orientation of the drive handle 114 does not differ between the two modes of operation. The change between each mode of operation or the singularity, as shown in FIGS. 5-7, occurs when the distal end 118 of the connecting link 116 pass through the pivot 136.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A gripping device comprising:
a first moveable jaw and a second fixed jaw;
a handle operatively engaged to the first moveable jaw and movable in a first direction;
a connecting link operatively engaged to the first moveable jaw, the connecting link positioned in at least one of a first position or a second position;
wherein, in the first position, the connecting link causes the first moveable jaw to move only inwardly relative to the second fixed jaw when the handle is moved in the first direction;
wherein, in the second position, the connecting link causes the first moveable jaw to move only outwardly relative to the second fixed jaw when the handle is moved in the first direction; and
wherein the handle includes an attachment point configured to engage a cable, wherein the attachment point remains in the same position when the connecting link is in the first position or in the second position.

2. The gripping device of claim 1, wherein a magnitude of a force exerted on the first moveable jaw is determined by a mode of operation for the device.

3. The gripping device of claim 2, wherein the mode of operation for the device is a voluntary open mode or a voluntary close mode.

4. The gripping device of claim 1, wherein the connecting link is positioned in the first position or the second position by a switch.

5. The gripping device of claim 4, wherein the switch is a bi-stable push-pull switch.

6. The gripping device of claim 4, wherein the switch comprises a position knob, wherein the position of the position knob determines the mode of operation of the gripping device when the switch is externally actuated.

7. The gripping device of claim 4, wherein the switch is a reciprocating push-push switch.

8. The gripping device of claim 1, wherein the first direction of the handle is inwardly relative to a user of the device.

9. The gripping device of claim 1, wherein the gripping device is adapted to be incorporated into a prehensor device.

10. The gripping device of claim 1, wherein the gripping device is adapted to be incorporated into a prosthetic hand.

11. The gripping device of claim 1, wherein the gripping device is adapted to be incorporated into a wrench or pliers.

12. The gripping device of claim 1, wherein the handle is movable using a Bowden cabling system.

13. A gripping device comprising:
a first moveable jaw and a second fixed jaw;
a handle operatively engaged to the first moveable jaw and moveable in a first direction; and
a lever operatively engaged to the first moveable jaw, the lever positioned in a first position or a second position by a switch;
wherein, when the lever is in the first position, complete actuation of the handle in the first direction causes the first moveable jaw to move only inwardly relative to the second fixed jaw;
wherein, when the lever is in the second position, complete actuation of the handle causes the first moveable jaw to move only outwardly relative to the second fixed jaw;
wherein, as the lever is moved into the first position by passing the switch through a singularity, the lever imparts a force that moves the first moveable jaw outwardly relative to the second fixed jaw.

14. The gripping device of claim 13, wherein the switch is a reciprocating push-push switch.

15. The gripping device of claim 13, wherein the switch is a bi-stable push-pull switch.

16. The gripping device of claim 13, wherein the switch comprises a position knob, wherein the position of the position knob determines the mode of operation of the gripping device when the switch is externally actuated.

17. The gripping device of claim 13, wherein the first direction of the handle is inwardly relative to a user of the device.

18. The gripping device of claim 13, wherein the gripping device is adapted to be incorporated into a prehensor device.

19. The gripping device of claim 13, wherein the gripping device is adapted to be incorporated into a prosthetic hand.

20. The gripping device of claim 13, wherein the gripping device is adapted to be incorporated into a wrench or pliers.

21. The gripping device of claim 13, wherein the handle is movable using a Bowden cabling system.

22. A gripping device comprising:
 a) a first moveable jaw and a second fixed jaw;
 b) a handle, rotatably engaged to a main body of the gripping device, the handle operatively engaged to the first moveable jaw and moveable in a first direction; and
 c) a lever having a first end operatively engaged to the first moveable jaw and a second end operatively engaged to the handle, the lever positioned in a first position or a second position;
 wherein, when the lever is in the first position,
  i) actuation of the handle in the first direction causes the first moveable jaw to move only inwardly relative to the second fixed jaw, and
  ii) release in actuation of the handle in the first direction results in the first moveable jaw moving to a default position outwardly relative to the second fixed jaw; and
 wherein, when the lever is in the second position,
  i) actuation of the handle in the first direction causes the first moveable jaw to move only outwardly relative to the second fixed jaw, and
  ii) release in actuation of the handle in the first direction results in the first moveable jaw moving to a default position inwardly relative to the second fixed jaw.

23. The gripping device of claim 22, further comprising a switch comprising a first member, the first member positioned in a channel of the switch assembly and operatively engaged to the connecting link; wherein the switch positions the lever in the first position or the second position.

24. The gripping device of claim 23, wherein the switch is a bi-stable push-pull switch.

25. The gripping device of claim 23, wherein the switch is a reciprocating push-push switch.

26. The gripping device of claim 22, wherein, as the lever is moved into the second position by passing the switch through the singularity, the lever imparts a force that moves the first moveable jaw inwardly relative to the second fixed jaw.

* * * * *